United States Patent [19]

Kawazoe et al.

[11] Patent Number: 5,277,200
[45] Date of Patent: Jan. 11, 1994

[54] PROBE HAVING A GIANT MAGNETOSTRICTIVE MATERIAL FOR ORGANISM DIAGNOSIS

[75] Inventors: Takayoshi Kawazoe, Nara; Keiji Saratani, Yao; Yoshinori Ishii, Kamakura; Norio Kaneko; Keiichi Kimura, both of Yokohama, all of Japan

[73] Assignee: Nikon Corporation, Tokyo, Japan

[21] Appl. No.: 937,706

[22] Filed: Sep. 1, 1992

[30] Foreign Application Priority Data

Sep. 4, 1991 [JP] Japan ................................ 3-253037

[51] Int. Cl.⁵ .............................................. A61B 5/10
[52] U.S. Cl. ........................................ 128/774; 73/575
[58] Field of Search ................. 128/774, 739, 660.01, 128/660.03, 661.03; 73/575

[56] References Cited

U.S. PATENT DOCUMENTS 4,754,763 7/1988 Doemland .................. 128/774 X
4,771,792 9/1988 Seale ............................. 128/774
4,819,753 4/1989 Higo et al. ..................... 128/739
5,195,532 3/1993 Schumacher et al. ......... 128/739

FOREIGN PATENT DOCUMENTS 62-172946 7/1987 Japan .

Primary Examiner—Francis Jaworski
Attorney, Agent, or Firm—Shapiro and Shapiro

[57] ABSTRACT

A probe has a vibration excitor including a core member made of a giant magnetostrictive material and magnetic field generation means for generating an alternating magnetic field having a randomly varying frequency to thereby expand and compress the core member to generate random vibration therein, and an impedance head for detecting an acceleration of the random vibration and a vibration stress created in organism tissue vibrated by the vibration excitor and generating electrical signals proportional thereto. A viscoelasticity measurement device using the above probe for the organism tissue is also disclosed.

9 Claims, 3 Drawing Sheets

PROBE HAVING A GIANT MAGNETOSTRICTIVE MATERIAL FOR ORGANISM DIAGNOSIS

BACKGROUND OF THE INVENTION

1. Field of the Invention

The present invention relates to a probe having a giant magnetostrictive material for organism diagnosis which is suitable for an instrument for diagnosing a viscoelasticity characteristic of organism tissue such as hardness of skin and swing of tooth.

2. Related Background Art

A mechanical impedance measurement device for a tooth as shown in FIG. 3 has been known as a diagnosing instrument. It comprises a random signal generator 31 for generating a random wave, a low pass filter 32, a power amplifier 33, a probe 34, a distortion amplifier 36, a charge amplifier 35 and a data processor 37. The probe 34 comprises a vibration exciter 41 which is driven by the output from the random signal generator 31, an impedance head 42 which is driven by the vibration of the vibration exciter 41 to vibrate a periodontium by random vibration and produces an electrical signal proportional to an acceleration of the random vibration and an electrical signal proportional to a vibration stress created in the periodontium vibrates by the random vibration, a tip 42a at an end of the head 42 and a load cell 43 for measuring a contact pressure (hereinafter static load) applied to the periodontium. The data processor 37 processes an electrical signal generated by the impedance head 42 and comprises an A/D converter 51, a personal computer 52 and a printer 53.

In the above mechanical impedance measurement device for tooth, the random wave from the random signal generator 31 is applied to the low pass filter 32, which supplies only components lower than a predetermined frequency (for example, 1 KHz) to the power amplifier 33, which amplifies the input random wave. The amplified random wave vibrates the vibration exciter 41 and the vibration thereof is transmitted to the impedance head 42 through the load cell 43 to vibrate the tip 42a. Because an affect of the static load developed between the periodontium and the tip 42a is large, the static load is measured by the load cell 43 to maintain the static load at a constant level. The static load measured by the load cell 43 is supplied to the strain amplifier 36 and amplified thereby, and the output thereof is sent to display means (not shown) to maintain the static load under measurement at the constant level.

On the other hand, when the tip 42a is contacted to the periodontium to vibrate the periodontium, the impedance head 42 produces a first electrical signal proportional to the acceleration of the input random wave and a second electrical signal proportional to the vibration strain from the vibrated periodontium. Those two electrical signals are amplified by the charge amplifier 35 and they are supplied to the data processor 37. In the data processor 37, they are converted to digital signals by the A/D converter 51 and they are applied to the personal computer and FFT-processed thereby. A transfer function of the system is determined by this process and it is converted to a viscoelasticity, (mechanical impedance) and displayed on a display on real time. It may be printed out by a printer, as may be required. The measurement data may be stored in memory means such as a floppy disk or transferred to other computer (host computer).

The probe of the measurement device uses a combination of an electromagnetic excitor (such as moving magnet or moving coil) or a vibration excitor using a piezo-electric device such as a PZT ($PbZrO_3$-$PbTiO_3$) ceramics, the impedance head and the mechanism for measuring the static load.

It is required to the probe that firstly it is compact, secondly it can be driven with a low voltage and a low current, thirdly it can provide a vibration up to a high frequency, and fourthly it can exactly measure the static load.

However, in the prior art electromagnetic vibration excitor described above, it is difficult to reduce the size while meeting the requirement for the vibration power and amplitude. Further, it can be used only in a low frequency band. Because of low axial rigidity of the vibration excitor, the attitude of the probe is unstable during the measurement and it is difficult to attain exact measurement of the static load. Further, in the vibration excitor which uses the piezo-electric device, the drive voltage and the drive current are large.

SUMMARY OF THE INVENTION

The present invention solves the above-problems by using giant magnetostrictive material as a vibration source for a probe.

According to the present invention, there is provided a probe having a giant magnetostrictive material for organism diagnosis, comprising:

a vibration excitor including a core member made of a giant magnetostrictive material and magnetic field generation means for generating an alternating magnetic field having a randomly varying frequency to thereby expand and compress said core member to generate random vibration therein; and an impedance head for detecting an acceleration of the random vibration and a vibration stress created in an organism tissue vibrated by said vibration excitor and producing electrical signals proportional thereto.

The giant magnetostrictive material is expressed by $RTx$, where R is at least one of rantanoid elements having atomic numbers 57-71, T is at least one transition element selected from Mn, Fe, Co and Ni, and x is atomic mol number which meets a relation of $0 \leq x \leq 9.0$.

Biasing means for applying a biasing magnetic field to a core member may be added. Adjustment means for adjusting a compression stress in an expansion/compression direction of the core member may also be added. Further, load measurement means for measuring a contact pressure between the organism tissue and the impedance head may be added.

In accordance with the present invention, the giant magnetostrictive material expressed by $RTx$ is used as the core material of the vibration excitor. Thus, a strain of no lower than 1000 ppm is generated with a small magnetic field (approximately 500 Oe at a room temperature), which is 10-1000 times as large as that of a prior art magnetostrictive material such as Ni alloy and 5-10 times as large as that of a piezo-electric device such as PZT, and an output thereof is very large compared to a piezo-electric ceramic such as PZT. Since the strain of the giant magnetostrictive material is varied by the change of the magnetic field, the device can be driven at a low voltage and a low current.

By using such a giant magnetostrictive material as the core material of the probe, the overall size is reduced, high vibration power with low drive current and voltage is attained and the vibration up to a high frequency is attained.

DETAILED DESCRIPTION OF THE PREFERRED EMBODIMENTS

Figure 1:
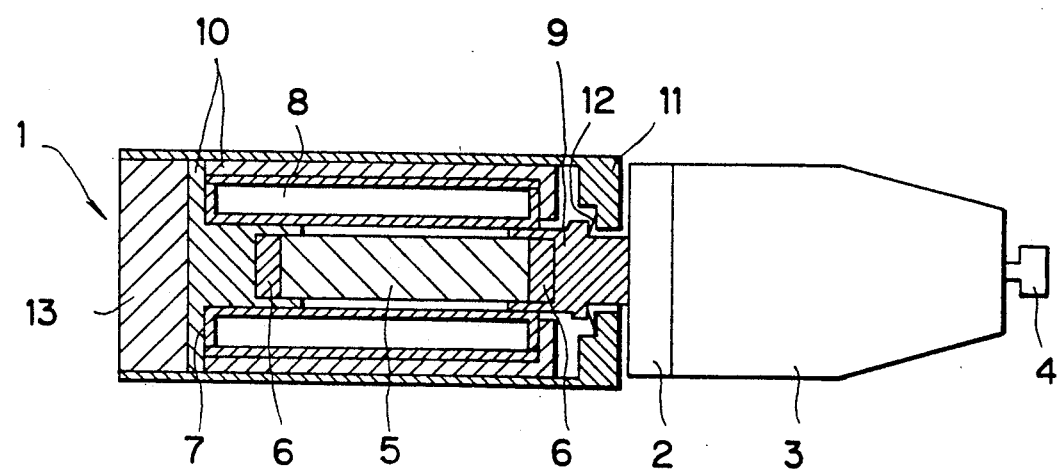
FIG. 1 shows one embodiment of a probe for organism diagnose using a giant magnetostrictive material in accordance with the present invention.
Figure 3:
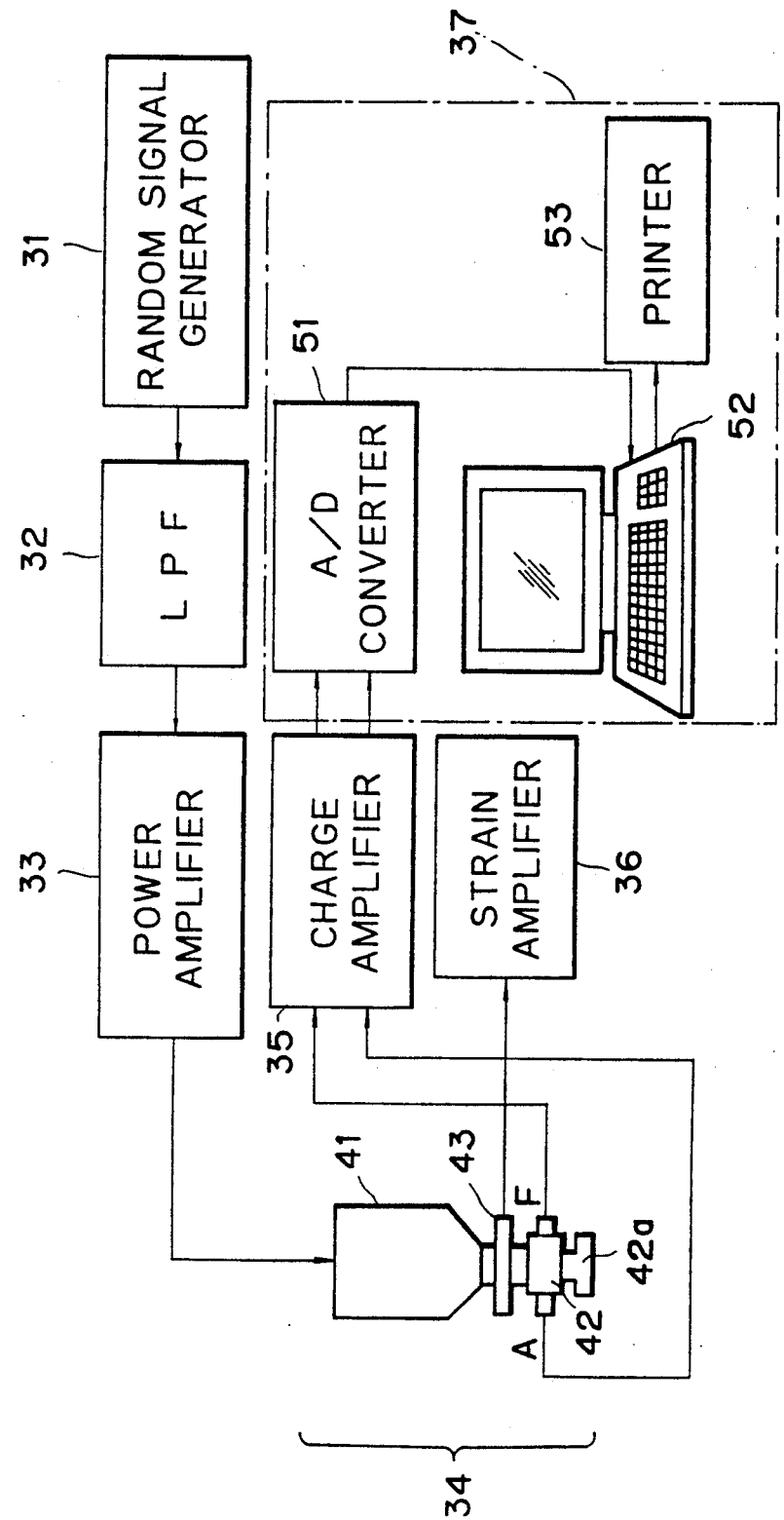
FIG. 3 shows a prior art mechanical impedance measurement device for a tooth.

An embodiment of the present invention is now explained with reference to the drawings. FIG. 1 shows a partial sectional view of the embodiment of the probe for the organism diagnosis having, the giant magnetostrictive material in accordance with the present invention. The present probe may be used in connection with the device shown in FIG. 3.

In the probe for the organism diagnosis of the present embodiment, an impedance head 3 is coupled to an output shaft 9 of a vibration excitor 1 through a load cell 2. The reason for providing the load cell 2 is for monitoring the output of the load cell 2 to maintain the contact pressure at a constant level because the affect of the contact pressure of the probe is large.

Provided at a center of the vibration excitor 1 is a core member 5 made of a $Tb_xDy_{1-x}Fe_2$ which is one of giantmagnetostrictive materials represented by RTx. A permanent magnet 6 for applying a biasing magnetic field to the core member 5 is arranged at the opposite ends of the core member 5. A coil 8 wound on a bobin 7 is arranged around the core member 5. A yoke 10 made of a magnetic material covers the core member 5, the permanent magnet 6, the bobin 7 and the coil 8 to prevent leakage magnetic fluxes therefrom.

A function of the biasing magnetic field is now explained. As shown, the giant magnetostrictive material assumes a positive distortion even if the polarity of the magnetic field is reversed. Thus, the distortion is minimum when a magnetic field strength H is zero. Accordingly, without the biasing magnetic field, the distortion C1 has afrequency 2f which is two times as high as a frequency of an input alternating current when the alternating current having the frequency f is applied to the coil 8 and the magnetic field strength is changed as shown by B1.

Figure 2:
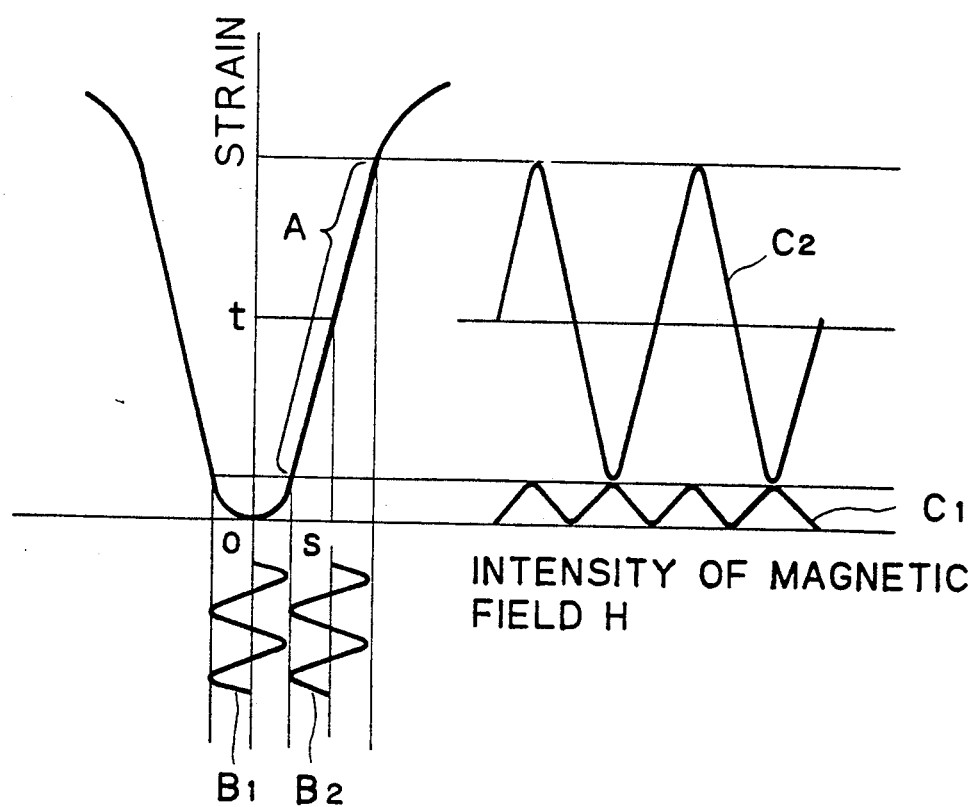
FIG. 2 shows a graph of a magnetic field strength and a strain of the giant magnetostrictive material used in the embodiment.

On the other hand, in a specific magnetic field strength region, the magnetic field strength and the strain have a substantially linear relation (shown by A). An appropriate biasing magnetic field S is applied in that region so that the core member 5 exhibits strain t at zero input. Under this condition, when the alternating current is applied to the coil 8 and the magnetic field is changed as shown by B2, the distortion changes as shown by C2. As seen from FIG. 2, the frequency at this time is equal to the frequency of the input alternating current and the amplitude (strain) is larger than that produced when no biasing magnetic field is applied.

The giant magnetostrictive material has a property of (i) the strain increases if a compression stress is preapplied, and (ii) a compression strength is high but a tensile strength is low. Thus, in the present embodiment, the output shaft 9 is attached to the end of the core member 5 and a spring 12 is inserted between the output shaft 9 and the case 11. As a result, a compression stress always acts on the core member 5 made of the giant magnetostrictive material and a large strain is produced.

Instead of the spring 12, the output shaft 9 at the end of the core member 5 and a case 11 may be linked by a low rigidity bolt and an elastic deformation of the bolt may be utilized. The case 11 is made of a non-magnetic material to prevent leakage magnetic flux.

A female thread is formed on an inner periphery of rear end of the case 11 and a male thread on an outer periphery of a rear cover 13 is screwed thereinto to compress the core member 5 so that the compression stress is varied.

In the present invention, since the respective components are linked together, the rigidity of the probe is enhanced. Thus, the static load can be measured by the load cell 2 with a high precision.

In the measurement, a signal having a randomly varying frequency is applied to the coil 8. As a result, the magnetic field changes in proportion to the signal in the vicinity of the core member 5. The distortion of the core member 5 changes with the change of the magnetic field so that the core member 5 makes random vibration. The vibration excites the organism tissue through the load cell 2 coupled to the output shaft 9 of the vibration excitor 1, the impedance head 3 and the tip 4.

The impedance head 3 measures the acceleration of the random vibration and the vibration stress created in the vibrated organism tissue and produces signals proportional thereto. The viscoelasticity of the organism tissue is diagnosed based on those signals.

Because of the above construction, the probe in the present invention is more compact than the prior art probe, and the amplitude of the vibration of the core member is larger so that the output signals are larger. The viscoelasticity measurement device for the organism tissue having the probe of the present invention can measure the viscoelasticity with a high precision.

In accordance with the present invention, since the core member of the vibration excitor is made of the giant magnetostrictive material, it is much compact than the prior art electromagnetic or piezo-electric core member for a given output power and a given amplitude, and it can be excited by a low current and a low voltage and produces a high power. Further, it permits exact measurement of the static load between the impedance head and the organism tissue.

What is claimed is:

1. A probe having a giant magnetostrictive material for organism diagnosis, comprising:
   a vibration excitor including a core member made of a giant magnetostrictive material and magnetic field generation means for generating an alternating magnetic field having a randomly varying frequency to thereby expand and compress said core member to generate random vibration therein; and
   an impedance head for detecting an acceleration of the random vibration and a vibration stress created in organism tissue vibrated by said vibration excitor and producing electrical signals proportional thereto.

2. A probe having a giant magnetostrictive material for organism diagnosis according to claim 1 further comprising biasing means for applying a biasing magnetic field to said core member.

3. A probe having a giant magnetostrictive material for organism diagnosis according to claim 1 further comprising adjusting means for adjusting a compression stress of said core member in an expansion/compression direction.

4. A probe having a giant magnetostrictive material for organism diagnosis according to claim 1 further comprising load measurement means for measuring a contact pressure between the organism tissue and the impedance head.

5. A viscoelasticity measurement device for organism tissue comprising:

a probe having a vibration excitor including a core member made of a giant magnetostrictive material and magnetic field generation means for generating an alternating magnetic field having a randomly varying frequency to thereby expand and compress said core member to generate random vibration therein;

an impedance head for detecting an acceleration of the random vibration and a vibration stress created by the organism tissue vibrated by said vibration excitor and producing electrical signals proportional thereto; and a data processor for fast-Fourier-transforming the electrical signal proportional to the acceleration of the random vibration and the electrical signal proportional to the vibration stress of the organism tissue, produced by said probe to determine a transfer function of a system under measurement and converting the same to a mechanical impedance of the organism tissue.

6. A viscoelasticity measurement device for organism tissue according to claim 5 wherein said probe further includes biasing means for applying a biasing magnetic field to said core member.

7. A viscoelasticity measurement device for organism tissue according to claim 5 wherein said probe further includes adjusting means for adjusting a compression stress of said core member in an expansion/compression direction.

8. A viscoelasticity measurement device for organism tissue according to claim 5 wherein said probe further includes load measurement means for measuring a contact pressure between the organism tissue and the impedance head.

9. A viscoelasticity measurement device for organism tissue according to claim 5 wherein said data processor is a personal computer.

* * * * *